US011298550B2

(12) United States Patent
Howard et al.

(10) Patent No.: US 11,298,550 B2
(45) Date of Patent: *Apr. 12, 2022

(54) USER INTERFACE FOR NEUROMODULATION LEAD

(71) Applicant: Boston Scientific Neuromodulation Corporation, Valencia, CA (US)

(72) Inventors: Joshua Dale Howard, Sacramento, CA (US); G. Karl Steinke, Valencia, CA (US); Richard Mustakos, Simi Valley, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 225 days.

This patent is subject to a terminal disclaimer.

(21) Appl. No.: 16/568,023

(22) Filed: Sep. 11, 2019

(65) Prior Publication Data

US 2020/0001097 A1 Jan. 2, 2020

Related U.S. Application Data

(63) Continuation of application No. 15/264,474, filed on Sep. 13, 2016, now Pat. No. 10,456,584.

(60) Provisional application No. 62/218,959, filed on Sep. 15, 2015.

(51) Int. Cl.
*A61N 1/372* (2006.01)
*A61N 1/05* (2006.01)
(Continued)

(52) U.S. Cl.
CPC ....... *A61N 1/37247* (2013.01); *A61N 1/0551* (2013.01); *A61N 1/3605* (2013.01); *G16H 40/63* (2018.01); *A61N 1/0534* (2013.01)

(58) Field of Classification Search
CPC .............. A61N 1/37247; A61N 1/0551; A61N 1/3605; G06F 19/3406
See application file for complete search history.

(56) References Cited

U.S. PATENT DOCUMENTS 7,650,184 B2 1/2010 Walter
8,019,439 B2 9/2011 Kuzma et al.
(Continued)

OTHER PUBLICATIONS

"U.S. Appl. No. 15/264,474, Final Office Action dated Mar. 8, 2019", 10 pgs.

(Continued)

*Primary Examiner* — Joseph M Dietrich
(74) *Attorney, Agent, or Firm* — Schwegman Lundberg & Woessner, P.A.

(57) ABSTRACT

Systems and methods for determining a parameter set and programming a neuromodulation system with the parameter set are disclosed. The system includes a user interface having a display screen to display simplified graphical representations (SGRs) of the lead with at least one virtual electrode (VE) that represents one or more electrodes, and control elements. The SGRs of the lead can provide longitudinal and circumferential representations of the VE, respectively representing longitudinal or circumferential position, size, shape, or spread of the VE. The control elements may include longitudinal and circumferential control elements to enable the user to respectively adjust the longitudinal or circumferential position, size, shape, or spread of the VE. The system may generate the neuromodulation parameter set using the longitudinal and circumferential representations of the VE, and program the neuromodulation system with the neuromodulation parameter set.

20 Claims, 9 Drawing Sheets

(51) Int. Cl.
*A61N 1/36* (2006.01)
*G16H 40/63* (2018.01)

(56) References Cited

U.S. PATENT DOCUMENTS

| | | |
|---|---|---|
| 8,380,321 B2 | 2/2013 | Goetz et al. |
| 8,875,391 B2 | 11/2014 | Pianca |
| 2012/0046715 A1 | 2/2012 | Moffitt et al. |
| 2014/0257428 A1 | 9/2014 | Zhu |
| 2017/0043172 A1 | 2/2017 | Stone et al. |
| 2017/0072207 A1 | 3/2017 | Howard et al. |

OTHER PUBLICATIONS

"U.S. Appl. No. 15/264,474, Non Final Office Action dated Aug. 8, 2018", 9 pgs.
"U.S. Appl. No. 15/264,474, Non Final Office Action dated Nov. 21, 2017", 10 pgs.
"U.S. Appl. No. 15/264,474, Non Final Office Action dated Dec. 5, 2017", 10 pgs.
"U.S. Appl. No. 15/264,474, Notice of Allowance dated Jun. 21, 2019", 5 pgs.
"U.S. Appl. No. 15/264,474, Preliminary Amendment dated Sep. 13, 2016", 3 pgs.
"U.S. Appl. No. 15/264,474, Response filed Mar. 1, 2018 to Non Final Office Action dated Dec. 5, 2017", 12 pgs.
"U.S. Appl. No. 15/264,474, Response filed May 8, 2019 to Final Office Action dated Mar. 8, 2019", 13 pgs.
"U.S. Appl. No. 15/264,474, Response filed Nov. 12, 2018 to Non Final Office Action dated Aug. 8, 2018", 12 pgs.
Buhlmann, J., et al., "Modeling of a segmented electrode for desynchronizing deep brain stimulation", Frontiers in Neuroengineering,, (Dec. 8, 2011), 1-8.
Martens, H. C.F., et al., "Spatial steering of deep brain stimulation volumes using a novel lead design", Clinical Neurophysiology, 122, (2011), 558-566.

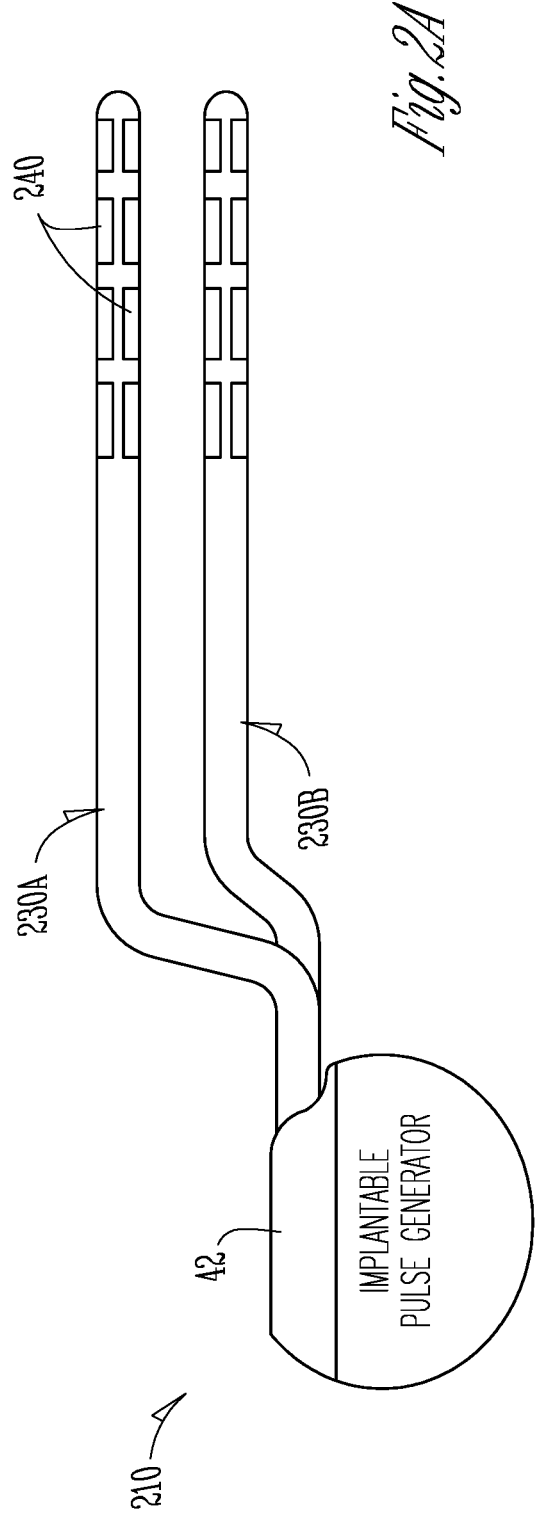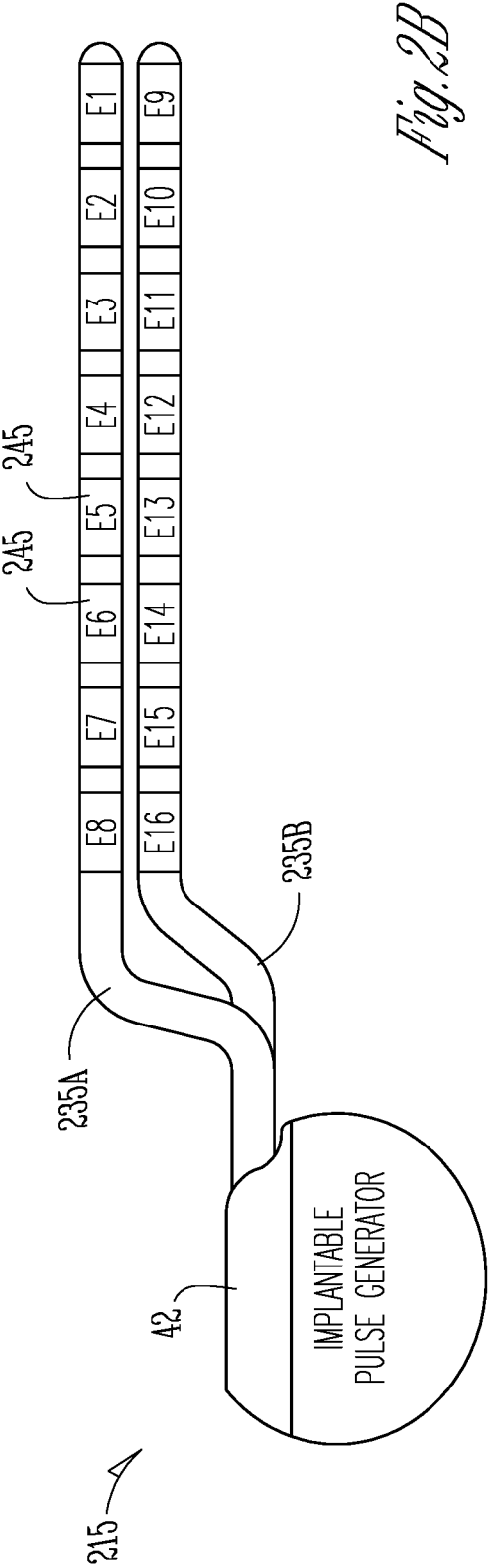

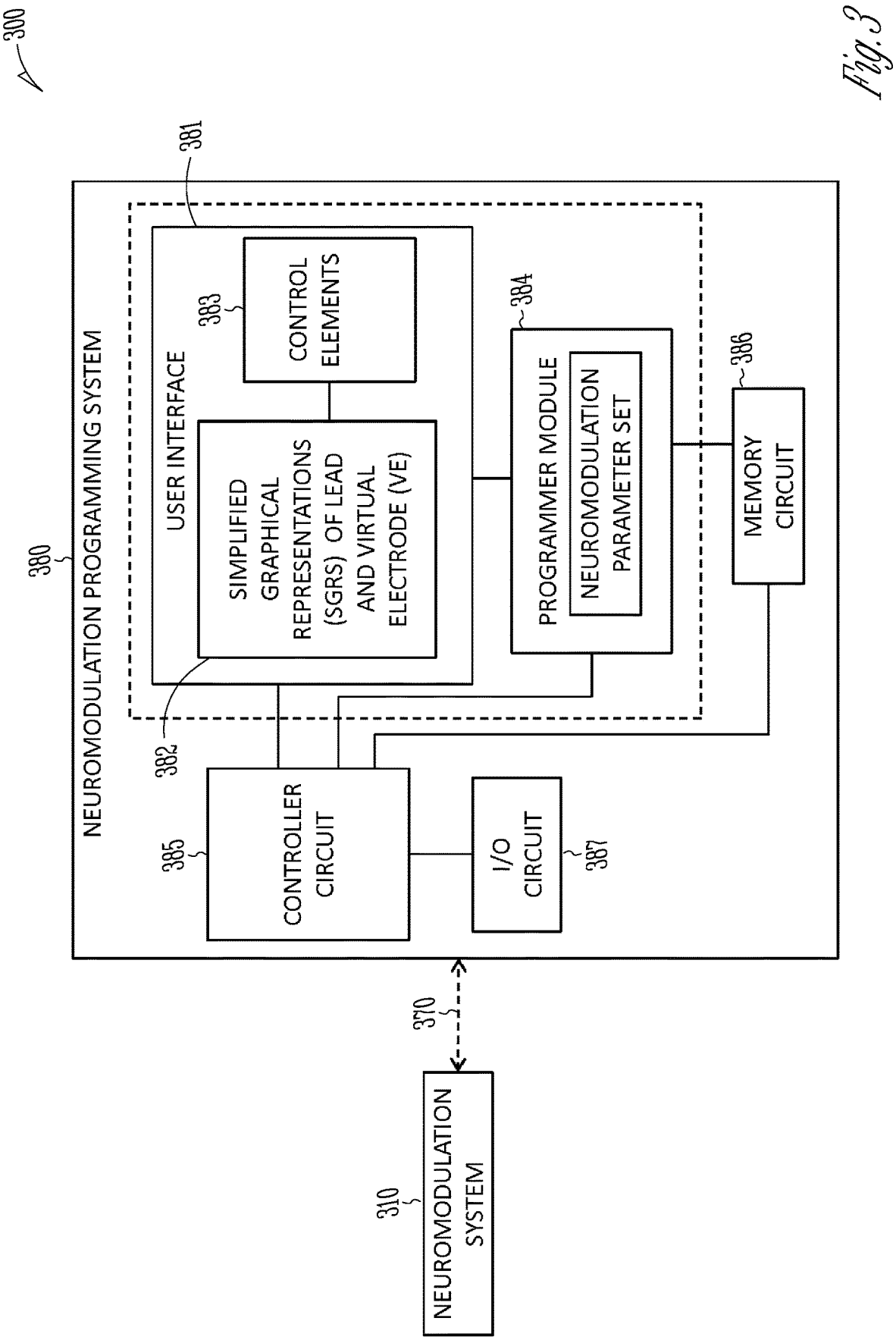

USER INTERFACE FOR NEUROMODULATION LEAD

CLAIM OF PRIORITY

This application us a continuation of U.S. application Ser. No. 15/264,474, filed Sep. 13, 2016, which claims the benefit of priority under 35 U.S.C. § 119(e) of U.S. Provisional Patent Application Ser. No. 62/218,959, filed on Sep. 15, 2015, each of which is herein incorporated by reference in its entirety.

TECHNICAL FIELD

This document relates generally to medical devices, and more particularly, to systems, devices, and methods for delivering neuromodulation to a neutral target.

BACKGROUND

Neuromodulation, also referred to as neuromodulation, has been proposed as a therapy for a number of conditions. Examples of neuromodulation include Spinal Cord Stimulation (SCS), Deep Brain Stimulation (DBS), Peripheral Nerve Stimulation (PNS), and Functional Electrical Stimulation (FES). Implantable neuromodulation systems have been applied to deliver such a therapy. An implantable neuromodulation system may include an implantable neuromodulator, also referred to as an implantable pulse generator, and one or more implantable leads each including one or more electrodes. The implantable neuromodulator may deliver neuromodulation energy through one or more electrodes placed on or near a target neural tissue. An external programming device may be used to program the implantable neuromodulator with parameters controlling the delivery of the neuromodulation energy.

OVERVIEW

Efficacy and efficiency of certain neuromodulation therapies may be affected by the electrode selection and fractionalized electrode configuration. Proper configuration of neuromodulation electrodes may allow the lead to be used to more accurately target a tissue that is desired to be modulated while avoiding or reducing undesirable side-effects caused by unintentionally modulating neighboring cell populations next to or around the target neural structures. Additionally, proper electrode selection and fractionalized electrode configuration may also reduce energy consumption and thereby extending longevity of the implantable neuromodulator.

Some neuromodulation systems, such as those used for DBS or SCS, may include leads that have a large number of electrodes available for stimulating neural targets. A lead may have a complex arrangement of multiple electrodes that not only are distributed axially along the leads, but are also distributed circumferentially around the lead. Such a lead, also known as a directional lead, presents a multitude of selections of modulation parameter sets to the clinician.

Current programming systems for determining modulation parameters typically include depictions of multiple electrodes on a display screen with actual geometric or physical properties of the electrodes, such as size, shape, dimension, position, orientation, inter-electrode spacing, among others. Information about electrode configurations and the modulation parameters are also displayed, such as electrode polarity, electrode combinations that define neuromodulation vectors, or fractionalized current distribution, among others. With increased number and complexity of electrodes in a lead (such as a directional lead), the amount of information presented to a system user, such as a clinician, may be overwhelming. As a result, programming of the neuromodulation system may become more complicated and time consuming. Embodiments of the present subject matter provide a programming system that may enable a system user to effectively and efficiently determine a neuromodulation parameter set, including select and configure electrodes for delivering neuromodulation to a neural target.

This document discusses, among other things, an embodiment of a system for use with a neuromodulation system that includes a lead having one or more electrodes at least partially surrounding a circumference of the lead for electrically modulating a target tissue of a patient. The system includes a user interface having a display screen to display simplified graphical representations (SGRs) of the lead with at least one virtual electrode (VE) that represents one or more electrodes, and control elements. The SGRs of the lead provide longitudinal and circumferential representations of the VE, respectively representing longitudinal or circumferential position, size, shape, or spread of the VE. The control elements may include longitudinal and circumferential control elements to enable the user to respectively adjust the longitudinal or circumferential position, size, shape, or spread of the VE. The system may generate the neuromodulation parameter set using the longitudinal and circumferential representations of the VE, and program the neuromodulation system with the neuromodulation parameter set.

In Example 1, a system for use with a neuromodulation system that includes a lead having one or more electrodes at least partially surrounding a circumference of the lead for electrically modulating a target tissue of a patient is disclosed. The system can comprise a user interface and a programmer module. The user interface can includes a display screen that can display simplified graphical representations (SGRs) of the lead with at least one virtual electrode (VE), and control elements that enable a user to adjust the SGRs of the lead. The SGRs can include one or more of at least a first view of the lead to provide a longitudinal representation of the VE representing a longitudinal position of the VE along a length of the lead, or at least a second view of the lead to provide a circumferential representation of the VE representing a circumferential position of the VE around at least a portion of a circumference of the lead. The control elements can include longitudinal control elements that enable the user to adjust the longitudinal representation of the VE including the longitudinal position of the VE along the length of the lead, and circumferential control elements that enable the user to adjust the circumferential representation of the VE including the circumferential position of the VE. The programmer module can be coupled to the user interface, and can use the longitudinal representation of the VE and the circumferential representation of the VE to generate a neuromodulation parameter set.

Example 2 can include, or can optionally be combined with the subject matter of Example 1 to optionally include, the display screen that can display the SGRs including the first view illustrating a longitudinal length of a portion of the lead, and the second view is a sectional view of the lead.

Example 3 can include, or can optionally be combined with the subject matter of one or any combination of Examples 1 or 2 to include, the display screen that can display the control elements that can include one or more view control elements to enable a user to select between at least the first and second views of the lead.

Example 4 can include, or can optionally be combined with the subject matter of one or any combination of Examples 1 through 3 to include, the display screen that can display the SGRs of the lead including two or more VEs. The control elements can include at least one VE activation control element to selectively activate, deactivate, show, or hide at least one of the two or more VEs.

Example 5 can include, or can optionally be combined with the subject matter of one or any combination of Examples 1 through 4 to include, the display screen that can display the first view of the lead including a representation of longitudinal size, shape, or spread of the VE along the length of the lead, and display the longitudinal control elements that enable the user to adjust the longitudinal size, shape, or spread of the VE.

Example 6 can include, or can optionally be combined with the subject matter of Example 5 to optionally include, the display screen that can display the longitudinal control elements including at least one longitudinal position icon with a longitudinal direction indicator, and at least one longitudinal spread icon with a longitudinal spread indicator. The longitudinal position icon can enable a user to incrementally adjust the longitudinal representation of the VE along the lead representation in a direction according to the at least one longitudinal direction indicator. The longitudinal spread icon can enable a user to incrementally adjust a longitudinal size, shape, or spread of the longitudinal representation of the VE in the first view.

Example 7 can include, or can optionally be combined with the subject matter of Example 5 to optionally include, the display screen that can display the longitudinal control elements that enable a user to adjust the longitudinal position using a selection and control method to select a first portion of the longitudinal representation of the VE and edit the longitudinal representation of the VE along the lead, and to adjust the longitudinal size, shape, or spread using the selection and control method to select a second portion of the longitudinal representation of the VE and edit an edge of the longitudinal representation of the VE along the lead to adjust a longitudinal dimension of the longitudinal representation of the VE in the first view.

Example 8 can include, or can optionally be combined with the subject matter of one or any combination of Examples 1 through 7 to include, the display screen that can display the longitudinal control elements that enable a user to adjust, in the first view, one or more of a polarity of the longitudinal representation of the VE, a neuromodulation vector configuration, or a distance between the longitudinal representation of the VE and a longitudinal representation of a reference electrode.

Example 9 can include, or can optionally be combined with the subject matter of one or any combination of Examples 1 through 8 to include, the display screen that can display the second view of the lead including a representation of circumferential size, shape, or spread of the VE around a circumference of the lead, and the circumferential control elements that enable the user to adjust the circumferential size, shape, or spread of the VE.

Example 10 can include, or can optionally be combined with the subject matter of Example 9 to optionally include, the display screen that can display the circumferential control elements including at least one circumferential position icon with a circumferential direction indicator, and at least one circumferential spread icon with a circumferential spread indicator. The circumferential position icon enables a user to incrementally rotate the circumferential representation of the VE around the circumference of the lead in a direction according to the circumferential direction indicator. The circumferential spread icon enables a user to incrementally adjust a circumferential size, shape, or spread of the circumferential representation of the VE in the second view.

Example 11 can include, or can optionally be combined with the subject matter of Example 9 to optionally include, the display screen that can display the circumferential control elements that enable a user to adjust the circumferential position using a selection and control method to select a first portion of the circumferential representation of the VE and edit the circumferential representation of the VE around the circumference of the lead. The circumferential control elements can enable a user to adjust the circumferential size, shape, or spread using the selection and control method to select a second portion of the circumferential representation of the VE and edit an edge of the circumferential representation of the VE around the circumference of the lead to adjust the circumferential dimension of the circumferential representation of the VE in the second view.

Example 12 can include, or can optionally be combined with the subject matter of one or any combination of Examples 1 through 11 to include, the display screen that can display the circumferential representation of the VE including a ring or an arc around the lead, and display the circumferential spread of the VE including an angle of the ring or the arc.

Example 13 can include, or can optionally be combined with the subject matter of one or any combination of Examples 1 through 12 to include, the programmer module that can determine the neuromodulation parameter set, including develop an electrode configuration and a fractionalized current distribution among at least some of the plurality of electrodes using the longitudinal representation of the VE and the circumferential representation of the VE.

Example 14 can include, or can optionally be combined with the subject matter of one or any combination of Examples 1 or 13 to include, a neuromodulation system that can include an electrostimulation generator and a programming system including the programmer module and the user interface. The electrostimulation generator can be operably connected to the neuromodulation lead to deliver neuromodulation using the lead. The programming system can be communicatively coupled to the neuromodulation system, and can program the neuromodulation system with the neuromodulation parameter set.

Example 15 can include, or can optionally be combined with the subject matter of Example 14 to optionally include, the neuromodulation system that can modulate a target neural tissue including a brain or a spinal cord using the lead.

In Example 16, a system can include a neuromodulation system and a programming system communicatively coupled to the neuromodulation system. The neuromodulation system can include an electrostimulation generator that can be operably connected to a lead having a plurality of electrodes along a longitudinal direction of the lead. At least some of the electrodes can be at least partially surrounding a circumference of the lead. The programming system can include a display screen that can be configured to display simplified graphical representations (SGRs) of the lead with at least one virtual electrode (VE), and control elements to enable a user to adjust the SGRs of the lead. The SGRs can include one or more of at least a first view of the lead or at least a second view of the lead. The first view can provide a longitudinal representation of the VE representing a longitudinal position of the VE along a length of the lead, and a longitudinal size, shape, or spread of the VE along the length of the lead. The second view can provide a circumferential representation of the VE representing a circumferential position of the VE around at least a portion of a circumference of the lead, and a circumferential size, shape, or spread of the VE around the circumference of the lead. The control elements can include longitudinal control elements and circumferential control elements. The longitudinal control elements enable the user to adjust the longitudinal representation of the VE including the longitudinal position and the longitudinal size, shape, or spread of the VE, and the circumferential control elements enable the user to adjust the circumferential representation of the VE including the circumferential position and the circumferential size, shape, or spread of the VE. The programming system can use the longitudinal representation of the VE and the circumferential representation of the VE to determine a neuromodulation parameter set, and program the neuromodulation system using the neuromodulation parameter set.

In Example 17, a method can be used for generating a neuromodulation parameter set to program a neuromodulation system that includes a lead having one or more electrodes at least partially surrounding a circumference of the lead for electrically modulating a target tissue of a patient. The method can include steps of providing a user interface that includes a display screen, and display on the display screen simplified graphical representations (SGRs) of the lead with at least one virtual electrode (VE), and control elements that enable a user to adjust the SGRs of the lead. The SGRs can include one or more of at least a first view of the lead that can provide a longitudinal representation of the VE representing a longitudinal position of the VE along a length of the lead, and a longitudinal size, shape, or spread of the VE along the length of the lead, or at least a second view of the lead that can provide a circumferential representation of the VE representing a circumferential position of the VE around at least a portion of a circumference of the lead, and a circumferential size, shape, or spread of the VE around the circumference of the lead. The control elements can include longitudinal control elements and circumferential control elements. The longitudinal control elements enable the user to adjust the longitudinal representation of the VE including the longitudinal position and the longitudinal size, shape, or spread of the VE. The circumferential control elements enable the user to adjust the circumferential representation of the VE including the circumferential position and the circumferential size, shape, or spread of the VE. The method can include steps of determining, for the at least one VE, one or more of a desired longitudinal position, a desired longitudinal size, shape, or spread, a desired circumferential position, a desired circumferential size, shape, or spread, and generating a neuromodulation parameter set using the longitudinal representation of the VE and the circumferential representation of the VE for delivering neuromodulation using the lead.

Example 18 can include, or can optionally be combined with the subject matter of Example 17 to optionally include, displaying the first view of the lead including a view illustrating a longitudinal length of a portion of the lead, and the second view including a sectional view of the lead, and displaying the control elements including one or more view control elements that enable a user to select between at least the first and second views of the lead.

Example 19 can include, or can optionally be combined with the subject matter of Example 17 to optionally include, displaying the longitudinal control elements including displaying at least one longitudinal position icon with a longitudinal direction indicator and at least one longitudinal spread icon with a longitudinal spread indicator. The longitudinal position icon enables a user to incrementally adjust the longitudinal representation of the VE along the lead representation in a direction according to the at least one longitudinal direction indicator. The longitudinal spread icon enables a user to incrementally adjust a longitudinal size, shape, or spread of the longitudinal representation of the VE in the first view.

Example 20 can include, or can optionally be combined with the subject matter of Example 17 to optionally include, displaying the longitudinal control elements that enable a user to adjust the longitudinal position using a selection and control method to select a first portion of the longitudinal representation of the VE and edit the longitudinal representation of the VE along the lead, and to adjust the longitudinal size, shape, or spread using the selection and control method to select a second portion of the longitudinal representation of the VE and edit an edge of the longitudinal representation of the VE along the lead to adjust a longitudinal dimension of the longitudinal representation of the VE in the first view.

Example 21 can include, or can optionally be combined with the subject matter of Example 17 to optionally include, displaying the circumferential control elements that include at least one circumferential position icon with a circumferential direction indicator, and at least one circumferential spread icon with a circumferential spread indicator. The circumferential position icon enables a user to incrementally rotate the circumferential representation of the VE around the circumference of the lead in a direction according to the circumferential direction indicator. The circumferential spread icon enables a user to incrementally adjust a circumferential size, shape, or spread of the circumferential representation of the VE in the second view.

Example 22 can include, or can optionally be combined with the subject matter of Example 17 to optionally include, displaying the circumferential control elements that enable a user to adjust the circumferential position using a selection and control method to select a first portion of the circumferential representation of the VE and edit the circumferential representation of the VE around the circumference of the lead, and to adjust the circumferential size, shape, or spread using the selection and control method to select a second portion of the circumferential representation of the VE and edit an edge of the circumferential representation of the VE around the circumference of the lead to adjust the circumferential dimension of the circumferential representation of the VE in the second view.

Example 23 can include, or can optionally be combined with the subject matter of Example 17 to optionally include, steps of programming the neuromodulation system with the neuromodulation parameter set, and delivering neuromodulation using neuromodulation system according to the neuromodulation parameter set.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense.

The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 2A-B illustrate, by way of example and not limitation, profile views of a neuromodulation system.

FIG. 3 illustrates, by way of example and not limitation, a portion of a neuromodulation system for modulating a target neural tissue.

DETAILED DESCRIPTION

Disclosed herein are systems and methods for determining a parameter set and programming a neuromodulation system with the parameter set. The neuromodulation system includes a lead having one or more electrodes at least partially surrounding a circumference of the lead for electrically modulating a target tissue of a patient. The disclosed system includes a user interface that may display simplified graphical representations (SGRs) of the lead with at least one virtual electrode (VE) that represents one or more electrodes, and control elements. The SGRs of the lead provide longitudinal and circumferential representations of the VE, respectively representing longitudinal or circumferential position, size, shape, or spread of the VE. A user may adjust the longitudinal or circumferential position, size, shape, or spread of the VE using the control elements. The simplified representation of the lead and the VE enables the user to more efficiently determine a neuromodulation parameter set to be programmed to the neuromodulation system.

Figure 1:
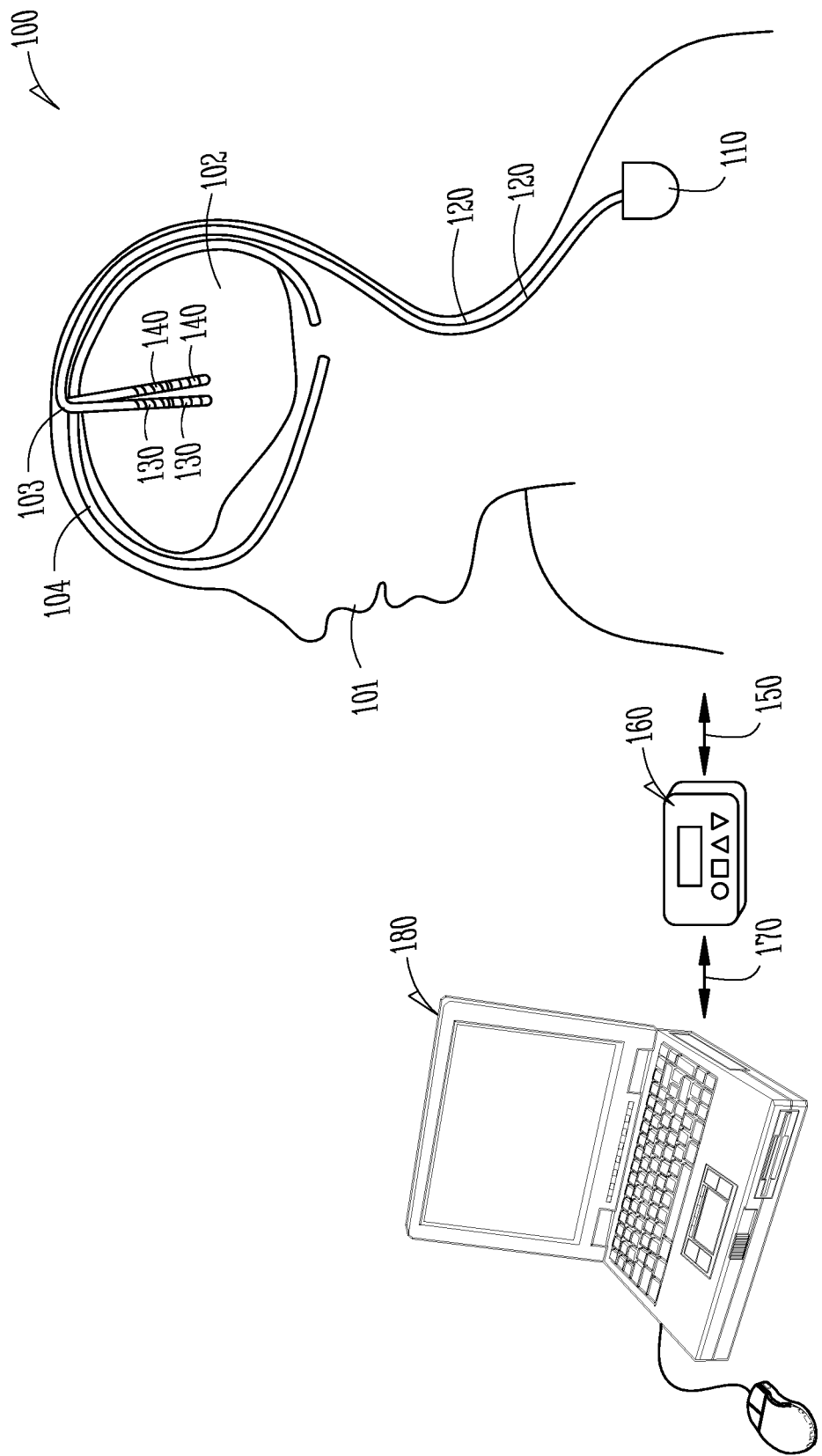
FIG. 1 illustrates, by way of example and not limitation, an example of an implantable neuromodulation system (INS) and portions of the environment in which the INS operates.

FIG. 1 illustrates, by way of example and not limitation, an example of an implantable neuromodulation system (INS) 100 and portions of the environment in which the INS 100 operates. In some embodiments the INS 100 may be used for deep brain stimulation (DBS) within a brain 102 of a patient 101. The INS may include an implantable pulse generator (IPG) 110, a lead system that includes leads 130 and lead extension 120 for delivering modulation pulses to target tissue, a programming system 180, and optionally an intermediate controller 160. The INS may be used to provide SCS or modulate other neural or muscular targets. For example, an SCS lead may be used to target a specific region of spinal cord tissue (which may include, by way of example and not limitation, dorsal column, dorsal horn, spinal nerve roots such as the dorsal nerve root, and dorsal root ganglia).

The IPG 110 may comprise a hermetically sealed outer case, also known as a "can", for housing a battery and pulse generation circuitry that delivers the electrical stimulation energy via one or more percutaneous lead extensions 120 to one or more leads such as a lead 130, which may carry a plurality of electrodes 140 distributed along the lead 130. The electrical stimulation energy may take in the form of a pulsed electrical waveform to the electrodes 140 in accordance with a set of modulation parameters programmed into the IPG 110. Electrical stimulation will occur between two or more activated electrodes, one of which may be the IPG case. Neuromodulation energy may be transmitted to the tissue in a unipolar or multipolar (e.g., bipolar, tripolar, etc.) configuration. Monopolar stimulation occurs when a selected one of the electrodes 140 is activated along with the case of the IPG 110, so that stimulation energy is transmitted between the selected electrode and the case. Bipolar stimulation occurs when two of the lead electrodes 140 are activated as anode and cathode, so that stimulation energy is transmitted between the selected electrodes 140. Tripolar stimulation occurs when three of the lead electrodes 140 are activated, two as anodes and the remaining one as a cathode, or two as cathodes and the remaining one as an anode.

The leads 130 may be introduced through a burr hole 103 (or alternatively, two respective burr holes) formed in the cranium 104 of the patient 101, and introduced into the parenchyma of the brain 102 of the patient 101 in a conventional manner, such that the electrodes 140 are adjacent a target tissue region, the stimulation of which will treat the dysfunction (e.g., the ventrolateral thalamus, internal segment of globus pallidus, substantia nigra pars reticulate, subthalamic nucleus, or external segment of globus pallidus). Stimulation energy may be conveyed from the electrodes 140 to the target tissue to change the status of the dysfunction. The IPG 110 may be implanted in a surgically-made pocket either in the chest, the abdomen, or other locations of the patient's body. The lead extension 130 facilitates locating the IPG 110 away from the exit point of the leads 130.

The programming system 180 may be communicatively coupled to the IPG 110, such as via a radio-frequency (RF) communications link (not shown). The programming system 180 may present to a system user, such as a clinician, neuromodulation parameters for programming the IPG 110, and enable the system user to program the IPG 110 using the neuromodulation parameters. Such neuromodulation parameters may include electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (which may be measured in milliamps or volts depending on whether the IPG 110 supplies constant current or constant voltage to the electrodes 140), pulse duration (which may be measured in microseconds), pulse rate (measured in pulses per second), and burst rate (which may be measured as the stimulation on duration X and stimulation off duration Y). The programming of the IPG 110 may be performed intraoperatively (e.g., during implant of the IPG 110 and/or the leads 130 in an operating room) or during a follow-up visit with the patient.

The programming system 180 may alternatively indirectly communicate with the IPG 10 through an intermediate controller, such as an external remote controller (RC) 160 that may telemetrically control the IPG 110 via a bi-directional communications link 150, such as a radio-frequency communication link. The programming system 180 may communicate with the RC 160 such as via an infrared communications link 170. The neuromodulation parameters provided by the programming system 180 may also be used to program the RC 160, so that the neuromodulation parameters may be subsequently modified by operation of the RC 160 in without the assistance of the programming system 180. In an example, the programming system 180, either alone or in combination with the RC 160, may control the operation of the IPG 110, such as turning on or off and programming the IPG 110 with different neuromodulation parameter sets to actively control the characteristics of the electrical modulation energy output by the IPG 110.

FIGS. 2A-B illustrate, by way of example and not limitation, profile views of neuromodulation system. FIG. 2A illustrates an implantable pulse generator (IPG) 210, which may be an embodiment of the IPG 110 as shown in FIG. 1, and two leads 230A and 230B configured to be operably connected to the IPG 210. Each of the lead may have a plurality of electrodes 240 that may be used for neuromodulation of a brain tissue. The illustrated leads 230A and 230B each includes an elongated cylindrical lead body, and the electrodes 240 take the form of segmented electrodes that are circumferentially and axially disposed about the lead body. In a non-limiting example, and as illustrated in FIG. 2A, the neurostimulation lead 230A or 230B may carry sixteen electrodes, arranged as four rings of electrodes, or four axial columns of electrodes. The actual number and shape of leads and electrodes may vary according to the intended application. Detailed description of construction and method of manufacturing percutaneous stimulation leads are disclosed in U.S. Pat. No. 8,019,439, entitled "Lead Assembly and Method of Making Same," and U.S. Pat. No. 7,650,184, entitled "Cylindrical Multi-Contact Electrode Lead for Neural Stimulation and Method of Making Same," the disclosures of which are incorporated herein by reference.

FIG. 2B illustrates an implantable pulse generator (IPG) 215, which may be an embodiment of the IPG 110 as shown in FIG. 1, and two leads 235A and 235B configured to be operably connected to the IPG 215. Each of the lead may have a plurality of electrodes 245 that may be used for neuromodulation of a region of a spinal cord. The leads 235A and 235B each includes an elongated cylindrical lead body and the electrodes 245 take the form of column electrodes (also known as ring electrodes) axially disposed along the length of the lead body. In a non-limiting example, and as illustrated in FIG. 2B, the leads 235A or 235B may carry eight electrodes along the lead body with specified electrode size, shape, and inter-electrode spacing.

FIG. 3 illustrates, by way of example and not limitation, an example of a portion of a neuromodulation system 300 for modulating a target neural tissue. The neuromodulation system 300 may be used for deep brain stimulation (DBS), spinal cord stimulation (SCS), a peripheral nerve stimulation (PNS), or stimulation of other neural targets or muscular targets. The neuromodulation system 300 may include a neuromodulation system 310 and a neuromodulation programming system 380.

The neuromodulation system 310 may include pulse generation circuitry that generate electrical stimulation energy, such as pulsed electrical waveform, and deliver the electrical stimulation energy to a neural target. Examples of the neuromodulation system 310 may include one of the IPGs 110, 210, or 215 as shown in FIGS. 1-2. The neuromodulation system 310 may be connected to one or more leads each carrying one or more electrodes, and deliver stimulation energy to the one or more electrodes in accordance with a set of modulation parameters programmed into the neuromodulation system 310.

The neuromodulation programming system 380 may be a dedicated hardware/software system, such as a programmer or a remote server-based patient management such as the programming system 180 as shown in FIG. 1. The neuromodulation programming system 380 may alternatively be defined predominantly by software running on a standard personal computer (PC). The neuromodulation programming system 380 may communicate with the neuromodulation system 310 via a communication link 370, such as an inductive telemetry link or a radio-frequency telemetry link. The neuromodulation programming system 380 may include one or more of a user interface 381, a programmer module 384, a controller circuit 385, a memory circuit 386, and an input/output (I/O) circuit 387.

The user interface 381 may include a display screen that may be configured, such as by the controller circuit 385, to display a simplified graphical representation (SGR) 382 of one or more leads, along with representation of one or more virtual electrodes (VEs) associated with the lead representation. The SGR of the lead is a "simplified" representation of an actual lead (such as leads 230A-b or 235A-B in FIGS. 2A and 2B), rather than a proportional depiction of the corresponding lead with actual physical size, shape, extent, or dimension. Likewise, a VE is a "simplified" representation of one electrode or an array of electrodes (such as electrodes 240 or 245 in FIGS. 2A and 2B), rather than a scaled depiction of an electrode with geometric or physical properties such as actual size, shape, spread, dimension, position or orientation with respect to the lead body, or inter-electrode spacing, among others. In an example, the SGR may include a two dimensional (2D) or a three dimensional (3D) graphical model of a directional lead associated with one or more VEs on the lead representation. The one or more VEs may include a 2D or 3D graphical representation of an individual or a combination of two or more electrodes, such as column electrodes (also known as ring electrodes, e.g., the electrodes 245 in FIG. 2B), or segmented electrodes circumferentially disposed on a directional lead (e.g., the electrodes 240 in FIG. 2A).

The SGR of the lead and the VEs may include graphical representation of a lead from a particular viewing perspective, such as one of a plurality of orthographic views, or a projection onto a specified plane. In an example, the SGR of the lead and the VE may include at least a first view and a second view of the lead. The first view may provide a longitudinal representation of the VE, which represents a longitudinal position of the VE along a length of the lead. In an example, the first view of the directional lead is an isometric view illustrating a longitudinal length of a portion of the directional lead. The second view may provide a circumferential representation of the VE representing a circumferential position of the VE around at least a portion of a circumference of the lead. In an example, the second view is a sectional view, such as a cross-sectional view, of the lead. Examples of the display of a SGR of a lead and the associated VEs are discussed below, such as with reference to FIGS. 4-7.

The display screen may be configured to additionally display a plurality of control elements 383. The control elements 383 may be shown as icons or bitmaps, optionally associated with text labels or markers indicating the function or manner of operation of the corresponding control elements. The control elements may include checkboxes, push buttons, radio buttons, or other user interface controls located on the display screen.

The control elements 383 enables a system user to adjust the SGR of the lead and VEs, such as: to activate or deactivate a SGR of a lead or a VE; to switch among various different views such as between the first view and the second view; to zoom, pan, rotate, or otherwise edit at least a portion of the SGR of the lead or a VE; or to adjust the position, shape, size, or focus or spread of one or more VEs. In an example, the user interface may include one or more input devices that enable the system user to adjust the SGR of the lead or the VEs on the display screen, such as by activating or navigating through the control elements 383. The input device may include a keyboard, on-screen keyboard, mouse, trackball, touchpad, touch-screen, or other pointing or navigating devices. Examples of the control elements for controlling a SGR of the lead and the associated VEs are discussed below, such as with reference to FIGS. 4-7.

The programmer module 384 may be coupled to the user interface 381 and configured to use the SGR of the lead and the VEs to generate a neuromodulation parameter set, and program the neuromodulation system 310 with the neuromodulation parameter set. The neuromodulation parameter set may include spatial information about neuromodulation, including electrode configuration, electrode combinations that define neuromodulation vectors, polarity of electrodes including electrodes that are activated as anodes (positive) or cathodes (negative) or being turned off, fractionalized electrode configurations indicating fractionalized distribution (e.g., percentage of stimulation energy) assigned to each electrode, among others. In an example, the programmer module 384 may generate the neuromodulation parameter set using a computational model or an anatomical model stored in the memory circuit 386. The computational or anatomical model may use the longitudinal representation of the VE and the circumferential representation of the VE, along with other parameters such as electrode-tissue properties, to estimate neuromodulation field established by electrodes represented by the VE and tissue responses to the neuromodulation, among others. The programmer module 384 may use the estimated neuromodulation field and other information to generate the neuromodulation parameter set. The programmer module 384 may be coupled to the memory circuit 386, which receives and stores the neuromodulation parameter set.

The I/O circuit 387 may include a telemetry circuit to output the neuromodulation parameter set to the neuromodulation system 310. The I/O circuit may also receive from the neuromodulation system 310 parameters indicating operational status of the pulse generator within the neuromodulation system 310, such as battery longevity indicators of the IND 110, lead impedance or lead integrity indicators of the lead 130, or physiological signals sensed by using one or more electrodes 140. The I/O circuit may also receive neuromodulation parameter set that has already been stored in the memory 386.

The controller circuit 385 may control the display of the SGR of the leads and the VE and the control elements, and adjustment of the displayed objects on the display screen in response to a user's input such as activating a control element via a user input device. The controller circuit 385 may control the programmer module 384 in generating the neuromodulation parameter set, and storing the neuromodulation parameter set in the memory circuit 386. In an example, the neuromodulation programming system 380 may program the neuromodulation system with at least the neuromodulation parameter set, such as via the communication link 370.

Figure 4:
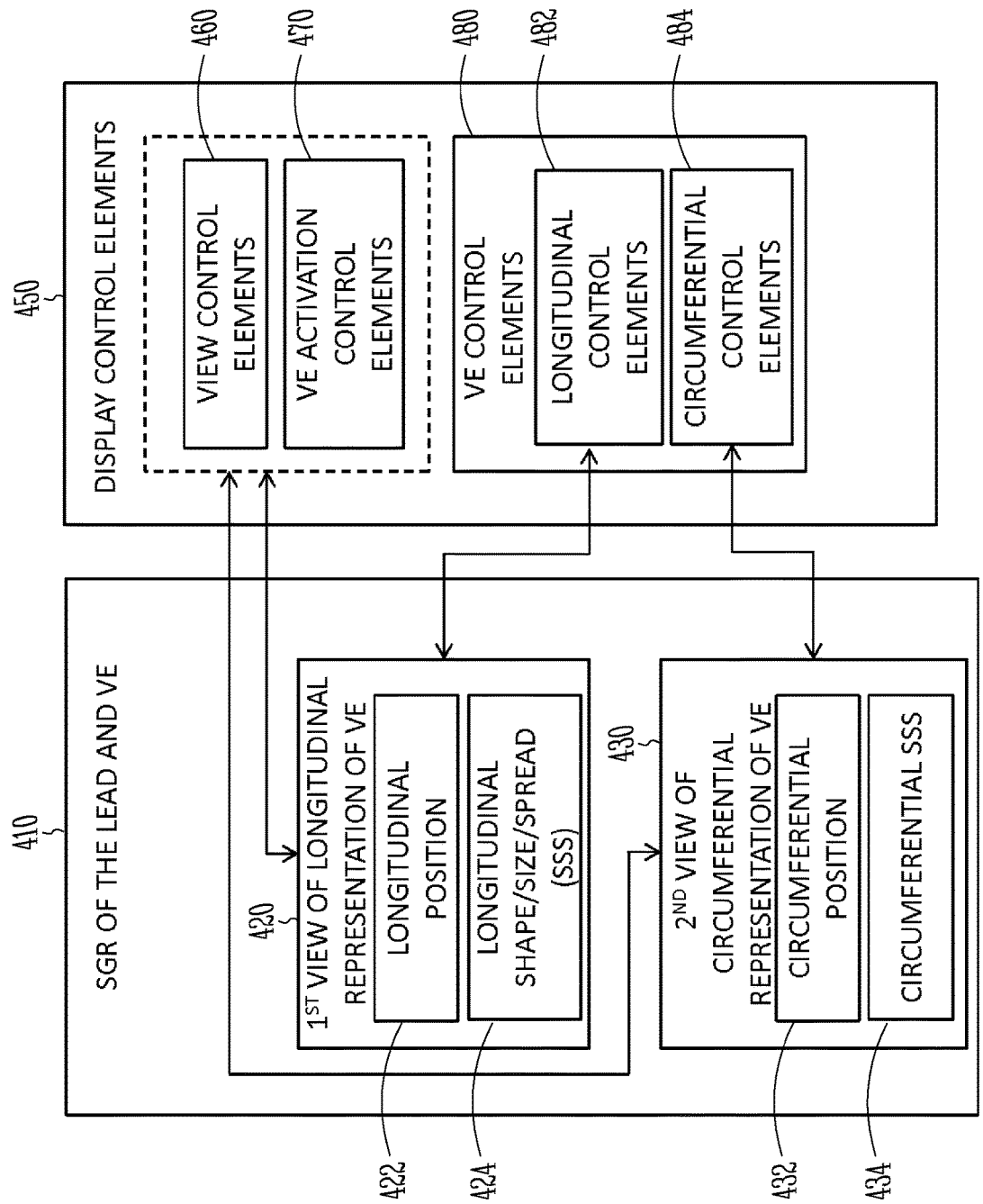
FIG. 4 illustrates, by way of example and not limitation, simplified graphical representations (SGRs) of one or more leads and the corresponding control elements.
Figure 8:
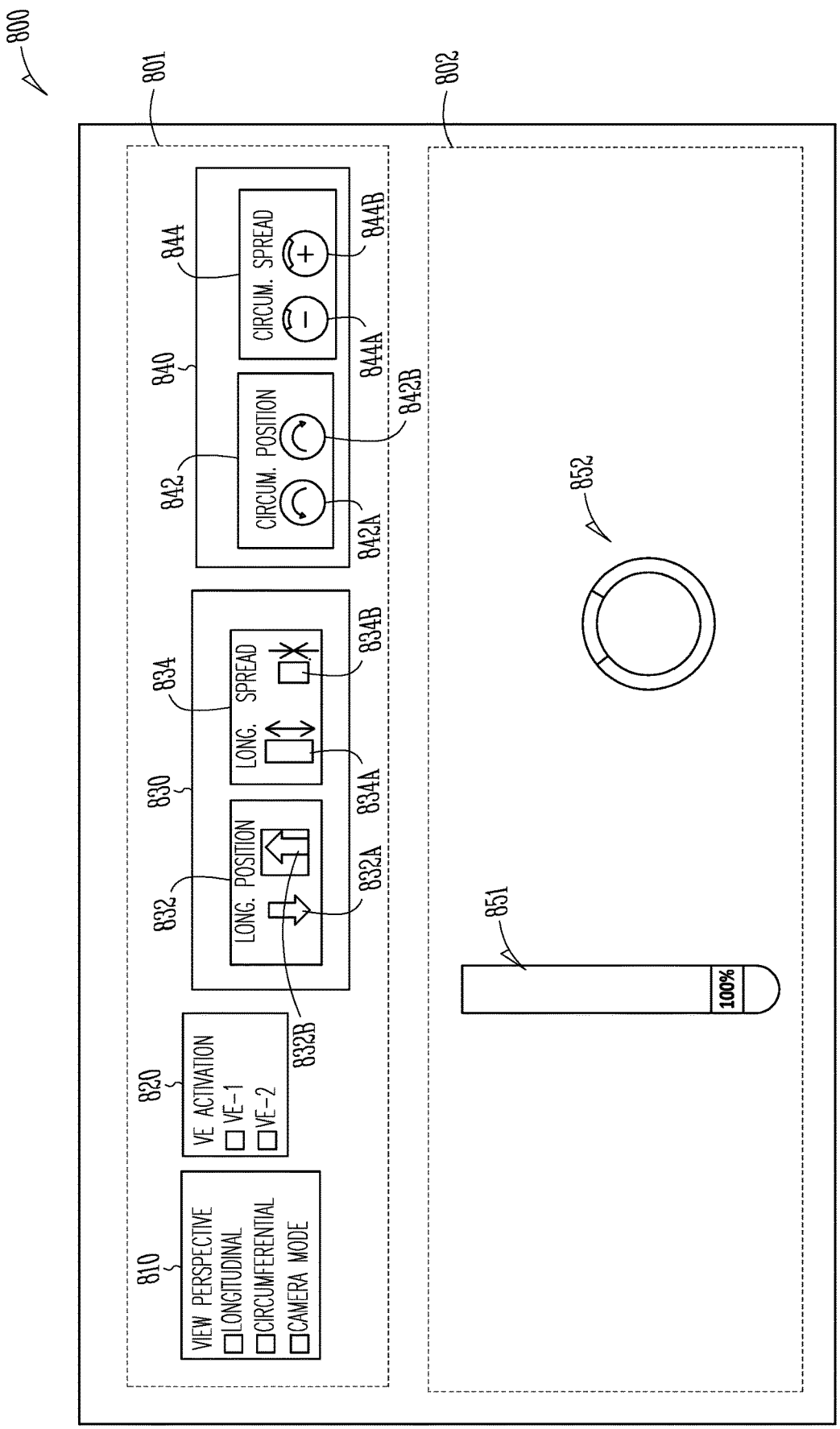
FIG. 8 illustrates, by way of example and not limitation, a plan view of at least a portion of a user interface.

FIG. 4 illustrates, by way of example and not limitation, an example of SGR of one or more leads and the associated VEs 410 and the corresponding control elements 450 for use by a system user to adjust the SGR of the leads and the VEs on a display screen. The SGR of the lead and VEs 410 and the control elements 450 may be displayed on a display screen. A system user may interactively adjust the display of the SGR of the lead and VEs 410 by using one or more of the control elements 450. By way of non-limiting examples, one or more SGRs with associated VEs, and the control elements for adjusting the SGRs or the VEs, may be displayed on the display screen in a plan view as illustrated in FIG. 8. The display may include a user control panel 801 to display various control elements, and a lead display zone 802 to display the SGRs of the lead and VEs. A system user may adjust the display of the SGR of the lead and VEs using the control elements on the user control panel 801, or alternatively or additionally using on-screen control to edit the SGR of the lead and VEs within the lead display zone 802.

Figures 5A, 5B:
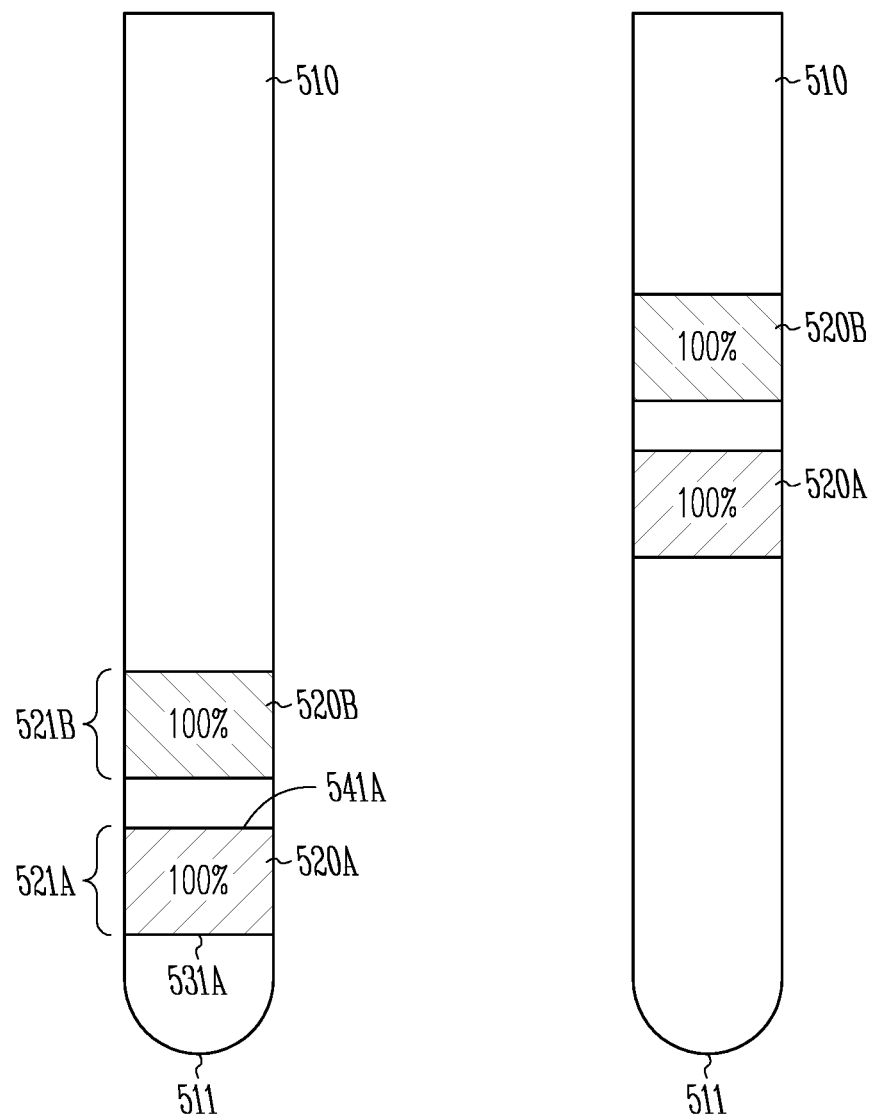
FIGS. 5A-B illustrate, by way of example and not limitation, SGRs of a lead with two virtual electrodes (VEs) displayed on a display screen.

The SGR of the lead and the VEs may include a first view 420 of longitudinal representation of the VE, and a second view 430 of circumferential representation of the VE. The first view 420 may provide a longitudinal position 422 of the VE along a length of the directional lead. By way of non-limiting example, and as illustrated in FIGS. 5A-B, SGRs of a lead 510 with a first VE 520A and a second VE 520B may be displayed on the display screen. The lead representation 510 is shown as a simplified 2D representation of a lead, and the two VEs 520A and 520B are shown as simplified 2D representation of actual neuromodulation electrodes. FIGS. 5A-B each shows different longitudinal positions of the VEs 520A and 520B, as indicated by a distance from a tip 511 of the SGR of the lead 510. The VEs 520A and 520B shown in FIG. 5A are disposed at more distal longitudinal positions (closer to the lead tip 511) than the respective VEs shown in FIG. 5B. Adjustment of the longitudinal positions of the VE, such as from the more distal positions shown in FIG. 5A to more proximal positions shown in FIG. 5B, may be achieved by activating one of the control elements, as will be discussed below with reference to FIG. 8.

In some examples, the first view 420 may additionally provide a longitudinal shape, size, or spread (SSS) 424 of the VE along the length of the directional lead. By way of non-limiting example, and as illustrated in FIGS. 5A-B, the VEs 520A and 520B have longitudinal shape of rectangles with respective heights 521A and 521B. The longitudinal SSS of a VE, such as the height 521A and 521B, may be indicative or correlative of the distribution of the electrical field established by the modulation current flowing from the electrodes to the neighboring tissue. Adjustment of the longitudinal SSS of the VE may be achieved by activating one of the control elements, as will be discussed below with reference to FIG. 8.

Figure 6B:
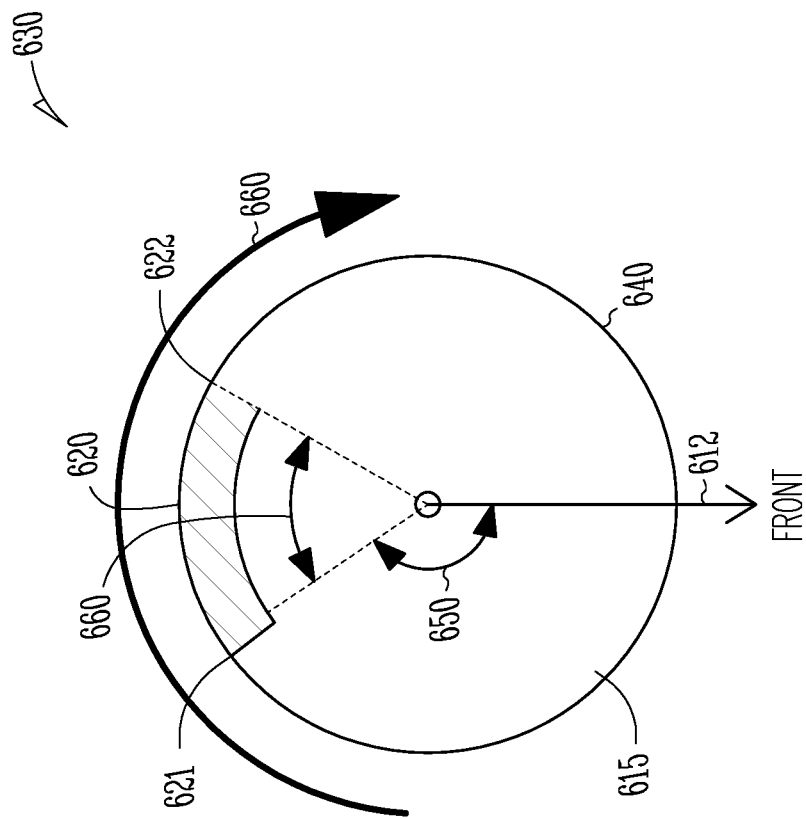
FIGS. 6A-B illustrate, by way of example and not limitation, SGRs of a lead with a VE in different views on a display screen.
Figure 6A:
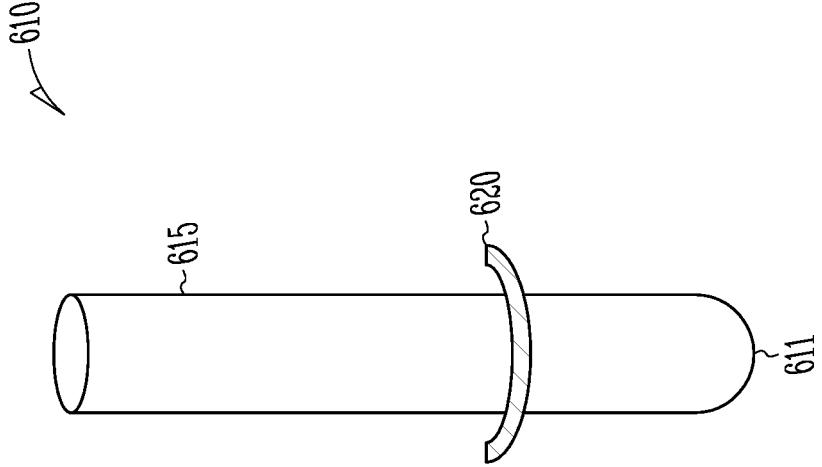

The second view 430 may provide a circumferential position 432 of the VE, representing a position of the VE around at least a portion of a circumference of the directional lead. By way of non-limiting example, and as illustrated in FIGS. 6A-B, a SGR of a lead 610 with a VE 620 can be displayed on the display screen. The VE 620 represents a segmented electrode circumferentially distributed around a portion of a circumference of the lead body 615. FIG. 6A illustrates a first view of the lead 610, which provides a longitudinal position of the VE 620, such as indicated by a distance from a tip 611 of the SGR of the lead 610. FIG. 6B illustrates a second view of the lead 610, which is a cross-sectional view 630. The VE in the cross-sectional view has a shape of an arc defined by two edges 621 or 622 around a circumference 640 of the lead 610. The second view provides a circumferential position of the VE 620, representing a position of the VE 620 around at least a portion of the circumference 640. The circumferential position may be represented by an angle of rotation 650 from a reference direction 612 (such as indicating a frontal direction of the lead 610) to a point on the VE 620 (such as an edge 621 or 622 on the VE 620). Adjustment of viewing perspectives of the SGR of the lead, such as activating or deactivating one view or change from a first view to a second view, are discussed below with reference to FIG. 8.

In some examples, the second view 430 may additionally provide a circumferential shape, size, or spread (SSS) of the VE around at least a portion of a circumference of the directional lead. The circumferential representation of a VE may have a shape of a ring or an arc around the directional lead. The ring-shaped VE may represent a column electrode such as the electrodes 245 as shown in FIG. 2B, or a combination of an array of segmented electrodes covering a full circumference around a lead. The arc-shaped VE (e.g., the VE 620 in FIG. 6B) may represent an individual segmented electrode, or a combination of several segmented electrodes covering a portion of a circumference around a lead, such as the electrodes 240 as shown in FIG. 2A.

Figure 7A:
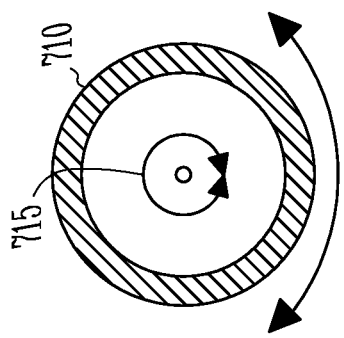
FIGS. 7A-C illustrate, by way of example and not limitation, VEs with different circumferential shapes and spreads on a cross-sectional view of a lead as displayed on a display screen.
Figure 7B:
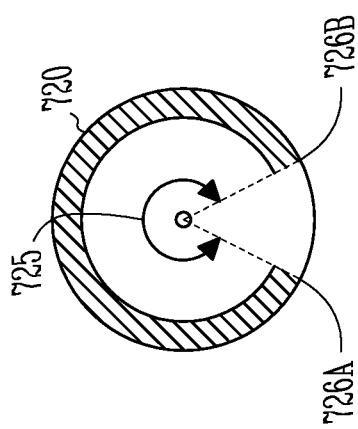
Figure 7C:
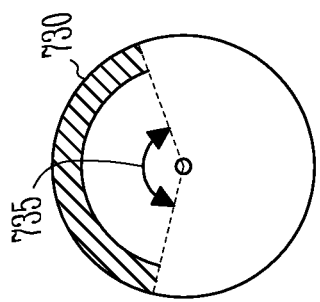

The circumferential SSS of a VE may be indicative or correlative of the distribution of the electrical field established by the modulation current flowing from the electrodes to the neighboring tissue. In an example, the circumferential spread of an arc-shaped VE (e.g., the VE 620 in FIG. 6B) can be measured as an angle of arc, such as angle 660 in FIG. 6B. A VE with a larger spread (e.g., a larger angle of arc of an arc-shaped VE 620) may correspond to less focused electrical field established by the modulation current. By way of non-limiting examples, and as illustrated in FIGS. 7A-C, cross-sectional views of VEs with different circumferential SSS can be displayed on the display screen. VE 710 in FIG. 7A has a circumferential shape of a ring, with a spread represented by an angle of arc 715 equal to 360 degrees. The VE 710 may represent a column electrode such as the electrodes 245 as shown in FIG. 2B, or an array of segmented electrodes around a full circumference of the lead. VE 720 in FIG. 7B has a circumferential shape of an arc with a spread represented by an angle of arc 725 less than 360 degrees and greater than 180 degrees. VE 730 in FIG. 7C has a circumferential shape of an arc with a spread represented by an angle of arc 735 less than 180 degrees. Therefore, the VE 710 has a full circumferential spread, or no focus, of the electrical field established in tissue neighboring the electrodes. The VE 720 represents an electrode or electrode combination with less circumferential spread, or more focus, than the VE 710. The VE 730 has the smallest angle of arc 735 among the three VEs shown in FIGS. 7A-C, and may represent an electrode or electrode combination with least circumferential spread, or highest level of focus. Adjustment of the circumferential SSS of the VE may be achieved by activating one of the control elements, as will be discussed below with reference to FIG. 8.

The SGRs of the leads and the associated VEs 410 may be adjusted by a user via a plurality of control elements 450 that may be displayed on the display screen. The control elements 450 may include view control elements 460, VE activation control elements 470, and VE control elements 480.

The view control elements 460 enables a system user to activate or deactivate a display of the SGR of the lead and the associated VEs shown in a particular viewing perspective, or to switch from one perspective to another different perspective. By way of non-limiting examples, the view control element 460 may include a view perspective box on the display screen, such as the view perspective box 810 on the control panel 801 in FIG. 8 that displays multiple viewing perspectives. The view perspective box 810 may include control buttons (e.g., checkboxes, radio buttons, or switch buttons) associated with respective text labels of "longitudinal" or "circumferential." The user may check the "longitudinal" checkbox to display the first view of a longitudinal representation of the VE (e.g., the VE 620 in FIG. 6A), or check the "circumferential" checkbox to display the second view of a circumferential representation of the VE (e.g., the VE 620 in FIG. 6B).

In an example, the view perspective box 810 may include a "camera mode" view perspective that enables the user to activate and edit the SGR of the lead to obtain continuously changing perspectives of the SGR of the lead. For example, the user may use a pointing device (e.g., a keyboard, an on-screen keyboard, a mouse, a trackball, a touchpad, a touch-screen), or other on-screen selection and control method, to activate and rotate the SGR of the lead. This effectually resembles imaging the SGR of the lead with a camera moving around within the space around a 3D SGR of the lead. Different views of the SGR of the lead, including the longitudinal and circumferential views, may be simultaneously displayed in accordance with the user's control. A desired view may be displayed as a still image through the user's control, such as via drag-and-drop operation of the SGR of the lead in the camera mode. In some examples, a selected view of the SGR of the lead, or any view obtained when the "camera" is set to a certain view under the "camera mode", may be augmented or adjusted. For example, in a circumferential view, certain portions of the SGR of the lead may be rendered transparent, or various UI changes may occur.

The VE activation control elements 470 enables a user to selectively activate, deactivate, show, or hide at least one of two or more VEs associated with the SGR of the lead. For an activated VE, the user may control one or more of position, size, shape, spread, or other properties of the activated VE. By way of non-limiting examples, the VE activation control element can include a VE activation box 820 on the control panel 801 in FIG. 8. The VE activation box 820 may include checkboxes associated with respective text labels of "VE-1" or "VE-2". The user may select a VE by checking the corresponding checkbox. Alternatively, the user may use a pointing device, or other on-screen selection and control method, to activate a VE, such as by pointing to or clicking on a VE using a pointing device.

The VE control elements 480 may include longitudinal control elements 482 and circumferential control elements 484. The longitudinal control elements 482 enable the user to adjust the longitudinal representation of the VE including the longitudinal position of the VE along the length of the directional lead such as in the first view (i.e., longitudinal view of the SGR of the lead).

The longitudinal control elements 482 may include at least one longitudinal position icon with a longitudinal direction indicator, which enables a user to incrementally adjust the longitudinal position of the VE along the lead representation (i.e., the longitudinal position 422 of the VE) in a direction according to the at least one longitudinal direction indicator. By way of non-limiting examples, the longitudinal control elements can include a "longitudinal position" box 832 displayed on the control panel 801 in FIG. 8. The longitudinal position" box 832 may include a first longitudinal direction icon 832A indicating a downward movement of the VE along the length of the lead, and a second longitudinal direction icon 832B indicating an upward movement of the VE along the length of the lead. To change the longitudinal positions of one or more VEs, such as moving the VEs 520A and 520B from their more distal positions (e.g., closer to the lead tip 511) shown in FIG. 5A to more proximal positions (e.g., farther away from the lead tip 511) in FIG. 5B, the user may activate one or both of the VEs 520A and 520B by checking the corresponding VE activation checkboxes, and then activate (e.g., clicking on or pressing) 832B until the selected VEs are shown on the display screen to move upward incrementally until they reach the desired longitudinal positions. The user may similarly move the longitudinal positions of the selected VEs downward toward the lead tip 511.

In some examples, the longitudinal control elements 482 enables a user to adjust the longitudinal position using a selection and control method to select a first portion of the longitudinal representation of the VE, and edit the longitudinal representation including the longitudinal position of the VE along the directional lead. For example, with reference to FIGS. 5A-5B, a user may be enabled to use a pointing device to point to, or touch at, a middle portion of the length of the VE to grab and drag the VE in a desired direction, such as moving the VE distally along the lead toward the tip 511, or proximally along the lead away from the tip 511.

The longitudinal control elements 482 may additionally or alternatively enable the user to adjust the longitudinal size, shape, or spread (SSS) of the VE. The longitudinal control elements 482 may include at least one longitudinal spread icon with a longitudinal spread indicator. The longitudinal spread icon enables a user to incrementally adjust a longitudinal dimension of the longitudinal representation of the VE such as in the first view (i.e., the longitudinal view of the SGR of the lead). By way of non-limiting examples, the longitudinal control elements can include a "longitudinal spread" box 834 on the control panel 801 in FIG. 8. The "longitudinal spread" box 834 may include a first longitudinal spread icon 834A indicating a lengthening of the VE along the length of the lead, and a second longitudinal spread icon 832B indicating a shortening of the VE along the length of the lead. To adjust the longitudinal SSS of a VE, such as to change the shape or height of one or both of the VEs 520A and 520B in FIGS. 5A-B, the user may activate the VEs such as by checking the corresponding VE activation checkboxes, and then activate (e.g., clicking on or pressing) 834A until the selected VEs are shown on the display screen to lengthen incrementally until they reach the desired longitudinal dimension. Similarly, the user may activate 834B to shorten the longitudinal dimension of the selected VEs.

In some examples, the longitudinal control elements 482 enables a user to adjust the longitudinal spread using a selection and control method to select a second portion of the longitudinal representation of the VE, and edit the longitudinal representation of the VE along the directional lead. For example, with reference to FIG. 5A, a user may be enabled to use a pointing device to point to, or touch at, an edge portion 531A or 541A of the longitudinal representation of the VE, and to grab and drag the VE 520A along the directional lead to adjust a longitudinal dimension of the longitudinal representation of the VE such as in the first view. For example, grabbing and dragging the edge 541A upwards may result in a lengthened VE 520A, while grabbing and dragging the edge 541A downwards towards the edge 531A may result in a shortened VE 520A.

The circumferential control elements 484 may enable the user to adjust the circumferential representation of the VE such as in the second view (e.g., a circumferential view of the SGR of the lead). The circumferential control elements 484 may include at least one circumferential position icon with a circumferential direction indicator. The circumferential position icon enables a user to incrementally adjust the circumferential position of the VE around the circumference of the directional lead in a direction according to the circumferential direction indicator. By way of non-limiting examples, the circumferential control elements can include a "circumferential position" box 842 displayed on the control panel 801 in FIG. 8. The "circumferential position" box 842 may include a first circumferential direction icon 834A indicating a counter-clockwise rotation of the VE around a circumference of the lead in a cross-sectional view of the VE, and a second circumferential direction icon 834B indicating a clockwise rotation of the VE around the circumference of the lead in the cross-sectional view of the VE. To adjust the circumferential position of a VE, such as reposition the VE 620 in a clockwise direction 660 as shown in FIG. 6B, the user may active (e.g., click on or press) 842B until the VE 620 are shown on the display screen to rotate clockwise incrementally around the circumference 640 until it reaches the desired circumferential position. Similarly, the user may activate 842A to rotate the VE 620 counter-clockwise around the circumference 640.

In some examples, the circumferential control elements 484 enable a user to adjust the circumferential position using a selection and control method to select a first portion of the circumferential representation of the VE, and edit the circumferential position of the VE around a circumference of the directional lead. For example, with reference to FIGS. 6A-B, a user may be enabled to use a pointing device to point to, or touch at, a middle portion of an arc-shaped VE 620 to grab and rotate the VE 620 in a desired rotational direction, such as clockwise or counter-clockwise.

The circumferential control elements 484 may additionally or alternatively enable the user to adjust the circumferential size, shape, or spread (SSS) of the VE. The circumferential control elements 484 may include at least one circumferential spread icon with a circumferential spread indicator. The circumferential spread icon enables a user to incrementally adjust a circumferential dimension of the circumferential representation of the VE such as in the second view (i.e., the circumferential view of the SGR of the lead). By way of non-limiting examples, the circumferential control elements can include a "circumferential spread" box 844 on the control panel 801 in FIG. 8. The "circumferential spread" box 844 may include a first circumferential spread icon 844A indicating a decrease in the circumferential spread around a circumference of the lead, and a second circumferential spread icon 844B indicating an increase in the circumferential spread around the circumference of the lead. To adjust the circumferential SSS of a VE, such as to reduce the spread of the VE 710 in FIG. 7, the user may activate (e.g., click on or press) 844A to incrementally decrease the angle of arc until a desired circumferential dimension is reached (e.g., the angle of arc is decreased from a first angle 715 to a second angle 725, or further down to a third angle 735). Similarly, the user may activate 844B to increase the circumferential spread of the VE.

In some examples, the circumferential control elements 484 enable a user to adjust the circumferential spread using a selection and control method to select a second portion of the circumferential representation of the VE, and edit the circumferential representation of the VE around a circumference of the directional lead. For example, with reference to FIG. 7B, a user may be enabled to use a pointing device to point to, or touch at, an edge portion 726A of the circumferential representation of the VE, and to grab and rotate the edge 726A clockwise around the circumference of the directional lead towards 726B to reduce the angle 725 and thereby reducing the circumferential spread of the VE 720.

Figure 9:
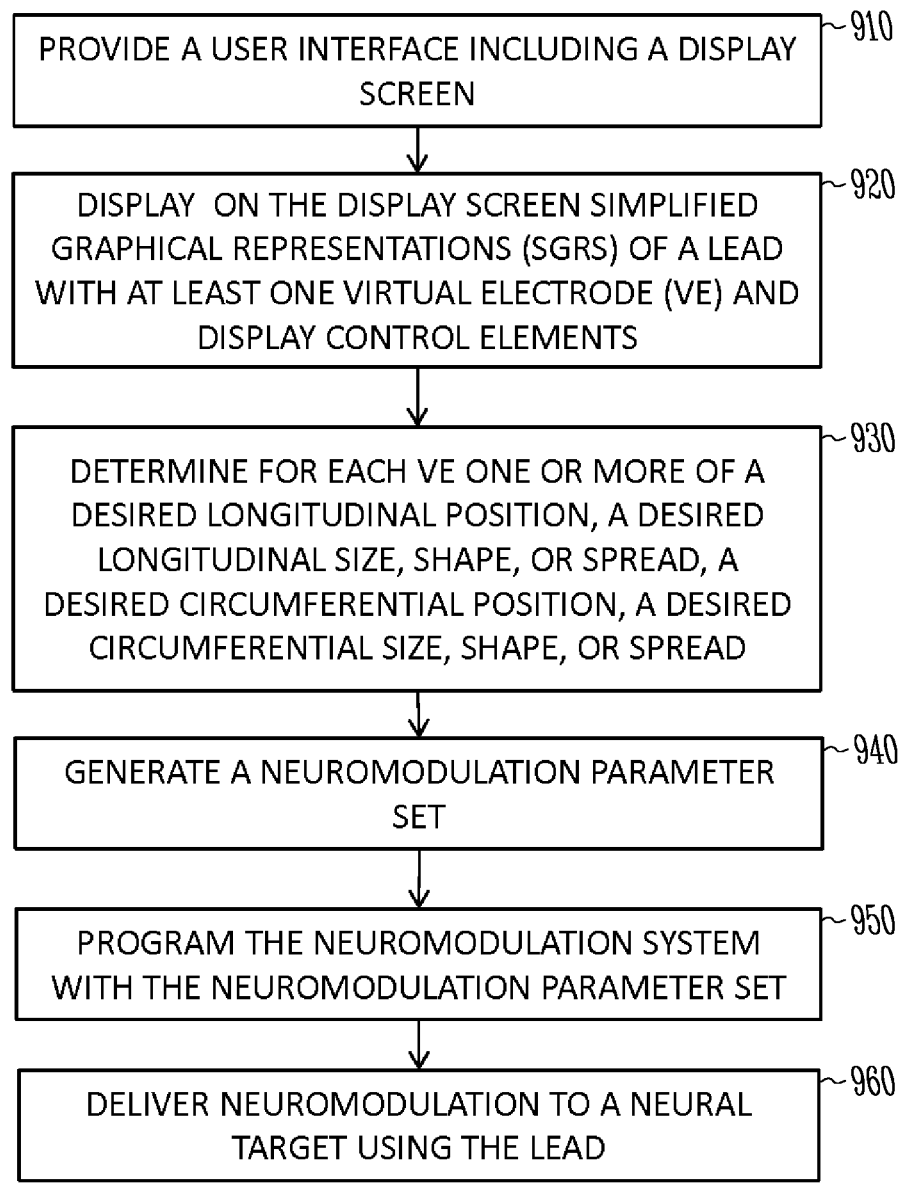
FIG. 9 illustrates, by way of example and not limitation, a method for creating and using SGRs of a lead to determine a neuromodulation parameter set.

FIG. 9 illustrates, by way of example and not limitation, an example of a method 900 for creating and using a SGR of a lead to determine a neuromodulation parameter set for programming a neuromodulation system and delivering neuromodulation to a neural target such as a brain, a spinal cord, or a peripheral neural tissue. The lead may be a directional lead that carries one or more segmented electrodes at least partially surrounding a circumference of the lead, such as the leads 230A and 230B shown in FIG. 2A. The lead may carry one or more column electrodes (also known as ring electrodes) axially disposed along the length of the lead body, such as the leads 235A and 235B shown in FIG. 2B. The method 900 may be implemented and operate in a medical system, such as the programming system 180 as shown in FIG. 1, or the neuromodulation system 300 as shown in FIG. 3, or any modification thereof. The method 900 may be used intraoperatively (e.g., during implant of a neuromodulation system in an operating room) or during a patient follow-up visit.

The method 900 begins at 910, where a user interface is provided. The user interface, such as the user interface 381 as shown in FIG. 3, may include a display screen configured to display simplified graphical representation (SGR) 382 of one or more leads along with representation of one or more virtual electrodes (VEs) associated with the lead representation.

At 920, the SGR of the one or more leads, along with the associated VEs, may be displayed on the display screen. The SGR of the lead is a "simplified" representation, rather than a proportional depiction of the corresponding lead with actual physical size, shape, extent, or dimension. The VE associated with the SGR of the lead is a "simplified" representation of one electrode or an array of electrodes, rather than a proportional depiction of the electrode(s) with actual geometric or physical properties such as size, shape, dimension, position or orientation such as with respect to a radial axis of the lead, or inter-electrode spacing, among others.

The SGR of the lead and the VEs may include graphical representation of a lead from a particular viewing perspective, such as one of a plurality of orthographic views, or a projection onto a specified plane. In an example, and as shown in the lead display zone 802 of FIG. 8, the SGR of the lead and the VE may include at least a first view and a second view of the lead. In an example, the first view of the directional lead is an isometric view illustrating a longitudinal length of a portion of the directional lead. The first view provides a longitudinal representation of the VE, which represents a longitudinal position of the VE along a length of the lead. The first view may additionally provide a longitudinal shape, size, or spread (SSS) 424 of the VE along the length of the directional lead, such as the VEs 520A and 520B each having a respective longitudinal shape of a rectangle with respective heights 521A and 521B. The longitudinal SSS of a VE may be indicative or correlative of the distribution of the electrical field established by the modulation current flowing from the electrodes to the neighboring tissue.

The second view provides a circumferential representation of the VE around at least a portion of a circumference of the lead. In an example, the second view is a sectional view of the lead, such as a cross-sectional view 630 of the lead 610, as shown in FIG. 6B. The second view may additionally provide a circumferential SSS of the VE around at least a portion of a circumference of the directional lead. The circumferential SSS of a VE, such as the spread as represented by an angle 660 of arc corresponding to the arc-shaped VE, may be indicative or correlative of the distribution of the electrical field established by the modulation current flowing from the electrodes to the neighboring tissue.

Also at 920 a plurality of control elements may be displayed on the display screen. The control elements, such as those displayed in the user control panel 801 shown in FIG. 8, may be shown as icons or bitmaps, optionally associated with text labels or markers indicating the function or manner of operation of the corresponding control elements. The control elements may be displayed as checkboxes, push buttons, radio buttons, or other UI controls located on the display screen. The control elements enable a system user to adjust the SGR of the lead and VEs.

At 930, a user is enabled to use the control elements to adjust the SGR of the lead and the VE as displayed on the display screen, and determine for each VE one or more of a desired longitudinal position, a desired longitudinal size, shape, or spread, a desired circumferential position, a desired circumferential size, shape, or spread. The control elements may include view control elements, VE activation control elements, and VE control elements which may further include longitudinal control elements and circumferential control elements. As previously discussed with respect to FIG. 8, the view control elements enable a system user to activate or deactivate a display of the SGR of the lead and the associated VEs shown in a particular viewing perspective, or to switch from one perspective to another different perspective. The VE activation control elements enable a user to selectively activate, deactivate, show, or hide one of two or more VEs associated with the SGR of the lead. Both the view control elements and the VE activation control elements may be used in the first, second, or any other user-specified view SGR of the lead.

The longitudinal control elements enable the user to adjust the longitudinal representation of the VE along the length of the directional lead such as in the first view (i.e., longitudinal view of the SGR of the lead), such as by adjusting the longitudinal positions of one or both of the VEs 520A and 520B in FIG. 5A to more proximal positions shown in FIG. 5B. The longitudinal control elements may additionally or alternatively enable the user to adjust the longitudinal size, shape, or spread (SSS) of the VE, such as lengthening or shortening the longitudinal dimension (or, height) of the VE 520A or 520B in FIGS. 5A-B. Adjustment of the longitudinal position or the longitudinal SSS may be achieved by activating corresponding control elements, such as the longitudinal position icons 832A-B or the longitudinal spread icons 834A-B as shown in FIG. 8, or by on-screen selection and control of the longitudinal representation of the VE, such as by using a pointing device to activate and edit the longitudinal representation of the VE on the display screen.

The circumferential control elements 484 enable the user to adjust the circumferential representation of the VE such as in the second view (e.g., a circumferential view of the SGR of the lead), such as by adjusting the circumferential positions of one or both of the VE 620 around a circumference of the lead in a cross-sectional view of the VE, as illustrated in FIG. 6B. The circumferential control elements may additionally or alternatively enable the user to adjust the circumferential SSS of the VE, such as reducing the circumferential spread of the VE 710 by decreasing the angle of arc 715 to a second angle 725, and further down to a third angle 735, until a desired circumferential dimension is reached. Adjustment of the circumferential position or the circumferential SSS may be achieved by activating corresponding control elements, such as the circumferential position icons 842A-B or the circumferential spread icons 844A-B as shown in FIG. 8, or by on-screen selection and control of the circumferential representation of the VE, such as by using a pointing device to activate and edit the circumferential representation of the VE on the display screen.

At 940, the SGR of the lead and the VEs may be used to generate a neuromodulation parameter set, such as by using the programmer module 384. The neuromodulation parameter set may include spatial information neuromodulation, including electrode configuration, electrode combinations that define neuromodulation vectors, polarity of electrodes including electrodes that are activated as anodes (positive) or cathodes (negative) or being turned off, fractionalized electrode configurations indicating fractionalized distribution (e.g., percentage of stimulation energy) assigned to each electrode, among others.

At 950, the neuromodulation parameter set may be programmed into the neuromodulation system, such as the neuromodulation system 310 in FIG. 3 or the IPG 110 in FIG. 1, via a communication link such as an inductive telemetry link or a radio-frequency telemetry link. At 960, neuromodulation energy (such as in a form of electrostimulation pulses) may be generated by the neuromodulation system and delivered to a neural target using the lead, in accordance with the neuromodulation parameter set.

In some examples, the method 900, or variants of any part of the method 900, may be implemented as instructions stored in a machine-readable storage medium. The machine may be in a form of a computer system, which may include a processor, memory, video display unit, an alpha-numeric input device, a user interface with a navigation device, a disk drive unit, a signal generation device, a network interface device, among others. The instructions may cause machine to perform any part of the method 900 or any variants thereof. The machine may operate as a standalone device or may be connected (e.g., networked) to other machines. While only a single machine is illustrated, the term "machine" shall also be taken to include any collection of machines that individually or jointly execute a set (or multiple sets) of instructions to perform any one or more of the methodologies discussed herein.

The machine-readable medium may include a single medium or multiple media (e.g., a centralized or distributed database, and/or associated caches and servers) that store the one or more instructions or data structures. The term "machine-readable storage medium" shall also be taken to include any tangible medium that is capable of storing, encoding or carrying instructions for execution by the machine and that cause the machine to perform any one or more of the methods of the present invention, or that is capable of storing, encoding or carrying data structures used by or associated with such instructions. The term "machine-readable storage medium" shall accordingly be taken to include, but not be limited to, solid-state memories, and optical and magnetic media. Specific examples of machine-readable media include non-volatile memory, including by way of example, semiconductor memory devices (e.g., erasable programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks. A "machine-readable storage medium" shall also include devices that may be interpreted as transitory, such as register memory, processor cache, and RAM, among others. The definitions provided herein of machine-readable medium and machine-readable storage medium are applicable even if the machine-readable medium is further characterized as being "non-transitory." For example, any addition of "non-transitory," such as non-transitory machine-readable storage medium, is intended to continue to encompass register memory, processor cache and RAM, among other memory devices.

In various examples, the instructions may further be transmitted or received over a communications network using a transmission medium. The instructions may be transmitted using the network interface device and any one of a number of well-known transfer protocols (e.g., HTTP). Examples of communication networks include a LAN, a WAN, the Internet, mobile telephone networks, plain old telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using combinations or permutations of those elements shown or described.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The scope of the invention should be determined with reference to the appended claims, along with the full scope of equivalents to which such claims are entitled.

What is claimed is:

1. A system for use with a neuromodulation system that includes a lead and physical electrodes disposed on the lead for electrically modulating a target tissue of a patient, the system comprising:
   a user interface including a display screen configured to display a graphical representation of the lead and graphical representations of first and second user-modifiable virtual electrodes (VEs) on the graphical lead representation, wherein:
   the first VE represents a virtual anode on the graphical lead representation, the virtual anode representing a combination of a plurality of physical electrodes on the lead used to deliver anodic energy; and
   the second VE represents a virtual cathode on the graphical lead representation, the virtual cathode representing a combination of a plurality of physical electrodes on the lead used to deliver cathodic energy; and
   a programmer, coupled to the user interface, configured to generate one or more neuromodulation parameters based at least on the graphical representations of the first and second VEs.

2. The system of claim 1, wherein the first and second VEs are positioned longitudinally apart along a length of the lead representation.

3. The system of claim 1, wherein the graphical representations of the first and second VEs include representations of one or more of:
   longitudinal positions of the first and second VEs along a length of the lead representation; or
   circumferential positions of the first and second VEs around at least a portion of a circumference of the lead representation.

4. The system of claim 1, wherein the graphical representations of the first and second VEs include representations of one or more of:
   longitudinal sizes, shapes, or spreads of the first and second VEs along a length of the lead representation; or
   circumferential sizes, shapes, or spreads of the first and second VEs around at least a portion of a circumference of the lead representation.

5. The system of claim 1, wherein the user interface includes a user control enabling a user to adjust the first or second VE, the adjusted first or second VE associated with the graphical lead representation.

6. The system of claim 5, wherein the user control includes a first control element for adjusting the first VE, and a separate second control element for adjusting the second VE.

7. The system of claim 5, wherein the user control includes one or more of:
   a longitudinal control element to enable longitudinal positioning of the first or second VE along a length of the lead representation; or
   a circumferential control element to enable circumferential positioning of the first or second VE around a circumference of the lead representation.

8. The system of claim 5, wherein the user control includes one or more of:
   a longitudinal control element to enable adjustment of longitudinal size, shape, or spread of the first or second VE; or
   a circumferential control element to enable adjustment of circumferential size, shape, or spread of the first or second VE.

9. The system of claim 1, wherein the one or more neuromodulation parameters generated by the programmer include one or more of:
   a fractionalized electrode configuration;
   an electrode activation and polarity; or
   a neuromodulation field parameter.

10. The system of claim 1, further comprising a neuromodulator configured to provide electrostimulation to the target tissue of the patient in accordance with the generated one or more neuromodulation parameters.

11. The system of claim 10, wherein:
    the programmer is configured to activate a first subset of the physical electrodes as anodes corresponding to the first VE, and to activate a second subset of the physical electrodes as cathodes corresponding to the second VE; and
    the neuromodulator is configured to provide electrostimulation to the target tissue of the patient via the activated first and second subsets of the physical electrodes.

12. The system of claim 11, wherein the first or second subset of the physical electrodes include segmented electrodes on the lead, and the electrostimulation provided by the neuromodulator includes deep brain stimulation.

13. A method for programming a neuromodulation system that includes a lead with associated physical electrodes to modulate a target tissue of a patient, the method comprising:
    providing a user interface that includes a display screen;
    displaying, on the display screen, a graphical representation of the lead and graphical representations of first and second user-modifiable virtual electrodes (VEs) on the graphical lead representation, wherein:
    the first VE represents a virtual anode on the graphical lead representation, the virtual anode representing a combination of a plurality of physical electrodes on the lead used to deliver anodic energy; and
    the second VE represents a virtual cathode on the graphical lead representation, the virtual cathode representing a combination of a plurality of physical electrodes on the lead used to deliver cathodic energy; and
    generating one or more neuromodulation parameters based at least on the graphical representations of the first and second VEs.

14. The method of claim 13, comprising providing electrostimulation to the target tissue of the patient in accordance with the generated one or more neuromodulation parameters.

15. The method of claim 14, wherein:
    generating one or more neuromodulation parameters includes activating a first subset of the physical electrodes as anodes corresponding to the first VE, and activating a second subset of the physical electrodes as cathodes corresponding to the second VE; and
    providing electrostimulation to the target tissue is through the activated first and second subsets of the physical electrodes.

16. The method of claim 13, wherein the graphical representations of the first and second VEs include representations of one or more of:

longitudinal positions of the first and second VEs along a length of the lead representation;

longitudinal sizes, shapes, or spreads of the first and second VEs along a length of the lead representation;

circumferential positions of the first and second VEs around at least a portion of a circumference of the lead representation; or circumferential sizes, shapes, or spreads of the first and second VEs around at least a portion of a circumference of the lead representation.

17. The method of claim 13, further comprising displaying, on the display screen, a user control enabling a use to adjust the first or second VE, the user control including one or more of:

a longitudinal control element to enable longitudinal positioning of the first or second VE along a length of the lead representation;

a longitudinal control element to enable adjustment of longitudinal size, shape, or spread of the first or second VE;

a circumferential control element to enable circumferential positioning of the first or second VE around a circumference of the lead representation; or a circumferential control element to enable adjustment of circumferential size, shape, or spread of the first or second VE.

18. The method of claim 13, wherein the one or more neuromodulation parameters includes one or more of:

a fractionalized electrode configuration;

an electrode activation and polarity; or a neuromodulation field parameter.

19. At least one non-transitory machine-readable medium including instructions that, when executed by a machine, cause the machine to:

display, on a display screen, a graphical representation of a lead and graphical representations of first and second user-modifiable virtual electrodes (VEs) on the graphical lead representation, wherein the first VE represents a virtual anode on the graphical lead representation, the virtual anode representing a combination of a plurality of physical electrodes on the lead used to deliver anodic energy, and the second VE represents a virtual cathode on the graphical lead representation, the virtual cathode representing a combination of a plurality of physical electrodes on the lead used to deliver cathodic energy; and generate one or more neuromodulation parameters based at least on the graphical representations of the first and second VEs.

20. The at least one non-transitory machine-readable medium of claim 19, wherein the instructions, when performed by the machine, cause the machine to:

activate a first subset of the physical electrodes as anodes corresponding to the first VE;

activate a second subset of the physical electrodes as cathodes corresponding to the second VE; and provide electrostimulation to target tissue via the activated first and second subsets of the physical electrodes in accordance with the generated one or more neuromodulation parameters.

* * * * *